United States Patent
Beden et al.

(10) Patent No.: US 7,044,432 B2
(45) Date of Patent: May 16, 2006

(54) FLUID CHANNEL VALVE FOR USE WITH A DISPOSABLE CARTRIDGE IN EXTRACORPOREAL CIRCULATIONS

(75) Inventors: Josef Beden, Mainz-Kastel (DE); Juergen Braun, Wahrheim (DE); Hans-Peter Schneider, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 188 days.

(21) Appl. No.: 10/363,703

(22) PCT Filed: Aug. 17, 2001

(86) PCT No.: PCT/EP01/09510

§ 371 (c)(1),
(2), (4) Date: Mar. 13, 2003

(87) PCT Pub. No.: WO02/25146

PCT Pub. Date: Mar. 28, 2002

(65) Prior Publication Data

US 2004/0084647 A1 May 6, 2004

(30) Foreign Application Priority Data

Sep. 20, 2000 (DE) .............................. 100 46 651

(51) Int. Cl.
*F16K 7/10* (2006.01)
(52) U.S. Cl. .................................................. 251/61.1
(58) Field of Classification Search ................. 251/61, 251/61.1, 61.2, 61.3, 61.4, 61.5, 331
See application file for complete search history.

(56) References Cited

U.S. PATENT DOCUMENTS

| 329,773 A | * | 11/1885 | Perry .......................... 138/93 |
| 2,886,281 A | * | 5/1959 | Canalizo ..................... 251/61.1 |
| 3,083,943 A | * | 4/1963 | Stewart, Jr. et al. ....... 251/61.1 |
| 3,556,465 A | * | 1/1971 | Little ......................... 251/61.1 |
| 3,689,025 A | * | 9/1972 | Kiser et al. ................ 251/61.4 |

(Continued)

FOREIGN PATENT DOCUMENTS

DE        26 28 238        1/1978

(Continued)

*Primary Examiner*—Eric Keasel
(74) *Attorney, Agent, or Firm*—Jacobson Holman PLLC

(57) ABSTRACT

A valve for the closure of fluid channels, in particular for use in disposable cartridges for extracorporeal circulations, having a valve body with a pressure channel, and a sealing cap, which can cooperate with the valve body in such a way that it closes off the end of the pressure channel on the valve body side against the surroundings. The valve is designed in such a way that a pressure chamber can be formed between the pressure channel and the sealing cap, and the sealing cap has a deformable sealing area for entry into a fluid channel in order to close the latter. The valve may be incorporated within a device for use with a disposable cartridge for at least one fluid channel.

19 Claims, 1 Drawing Sheet

U.S. PATENT DOCUMENTS

| | | | | |
|---|---|---|---|---|
| 4,178,940 A | | 12/1979 | Au | 128/207.15 |
| 4,333,452 A | | 6/1982 | Au | 128/205.24 |
| 4,662,598 A | * | 5/1987 | Weingarten | 251/61.1 |
| 4,705,259 A | * | 11/1987 | Dolhen et al. | 251/61.1 |
| 5,178,182 A | | 1/1993 | Kamen | 137/454.2 |
| 5,609,572 A | | 3/1997 | Lang | 604/22 |
| 5,769,387 A | * | 6/1998 | Perez | 251/61.1 |
| 5,775,371 A | | 7/1998 | Pan et al. | 137/597 |
| 6,053,191 A | * | 4/2000 | Hussey | 251/61.1 |
| 6,189,857 B1 | * | 2/2001 | Zeger et al. | 251/61.1 |

FOREIGN PATENT DOCUMENTS

| | | |
|---|---|---|
| DE | 28 27 648 | 1/1979 |
| DE | 40 06 785 | 9/1990 |
| DE | 43 36 336 | 5/1994 |
| DE | 696 18 766 | 8/2002 |
| EP | 0 848 193 | 6/1998 |
| GB | 1 483 702 | 8/1977 |
| GB | 2 331 796 | 6/1999 |
| JP | 08028722 | 2/1996 |
| WO | 94/20155 | 9/1994 |

* cited by examiner

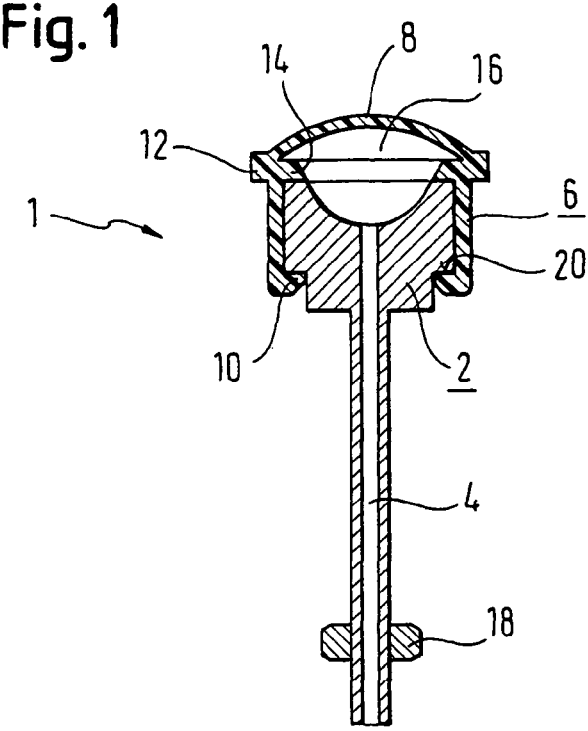
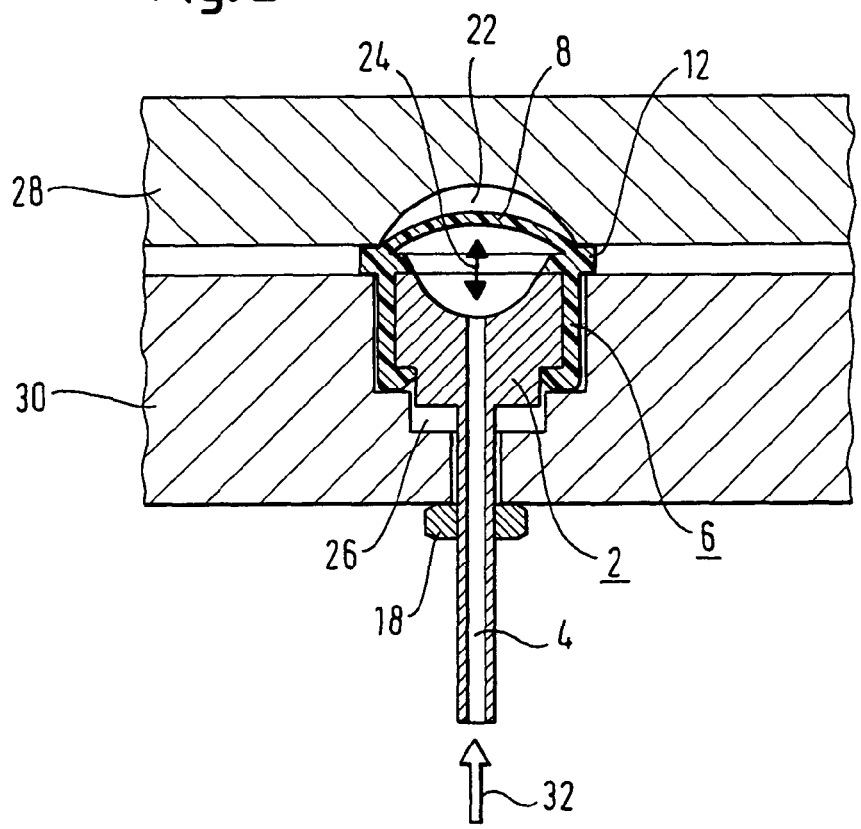

FLUID CHANNEL VALVE FOR USE WITH A DISPOSABLE CARTRIDGE IN EXTRACORPOREAL CIRCULATIONS

This is a nationalization of PCT/EP01/09510 filed Aug. 17, 2001 and published in German.

BACKGROUND OF THE INVENTION

1. Field of the Invention

The present invention relates to a valve for the closure of fluid channels, in particular for use with disposable cartridges for extracorporeal circulations, such as for example in dialysis.

2. Description of the Related Art

Such valves are used to permit or to stop the fluid flow in dialysis systems. So-called disposable cartridges or one-time cartridges include in the cartridge body liquid channels which have to be opened or closed depending on the requirement of the treatment, in order to convey or interrupt the dialysis liquid. The liquid channels of the cartridge body can be closed off with a disposable film. The disposable cartridge is closed with a counterpart on the device side, which counterpart is pressed, e.g. screwed down, with the disposable cartridge. In this way, the fluid channels of the disposable cartridge are closed off against the surroundings.

The components, which come into contact with blood or dialysis liquid as the case may be, must satisfy high hygiene requirements.

With a disposable cartridge described in WO 94/20155, several fluid channels are stamped in a body of this cartridge. At a point at which it is intended to be able to interrupt the fluid flow, projections are provided in the fluid channel. The fluid channels of the body are closed with a counterpart on the device side. In the area of the projections, this counterpart has flexible areas which can be pressed against the projections in the fluid channel. In this way, the fluid flow can be interrupted.

The problem of the present invention is to provide a valve and its application, in particular for use with a disposable cartridge, which are able to satisfy the hygiene requirements in a cost-effective and simple manner.

SUMMARY OF THE INVENTION

This problem is solved according to the present invention with a valve for the closure of fluid channels, in particular for use with disposable cartridges for extracorporeal circulations. The valve includes a valve body with a pressure channel, and a sealing cap which cooperates with the valve body in such a way that it closes off the end of the pressure channel on the valve body side against the surroundings. The valve is designed in such a way that a pressure chamber can be formed between the pressure channel and the sealing cap, whereby the sealing cap has a sealing area that is deformable in such a way that a fluid channel can be closed thereby. The present invention is further directed to a disposable cartridge having at least one fluid channel, and to a device for use with such a disposable cartridge, in which the fluid flow rate through such channel is controlled by a valve of the type just described.

The valve according to the invention has a valve body with a pressure channel. A sealing cap co-operates with the valve body in such a way that the end of the pressure channel on the valve body side closes against the surroundings. A pressure chamber can be formed between the pressure channel and the sealing cap, whereby a deformable sealing area of the sealing cap can enter into the liquid channel in order to close the latter.

The sealing cap can be rigidly connected to the valve body. A sealing cap which is detachable from the valve body, however, is particularly user-friendly and maintenance-friendly. This additionally simplifies and reduces the cost of the replacement of the sealing cap of importance for hygiene.

The valve function can easily be monitored by checking the pressure in the pressure channel of the valve. By applying an excess pressure on the pressure channel, the liquid channel is closed by the stretching of the deformable area. Simple venting in the pressure channel or the application of a partial vacuum opens the valve. The deformable valve cap provides for a good tolerance compensation both with the depth of the channel as well as with lateral misalignment of the valve with respect to the liquid channel.

Finally, the overall, simply constructed valve unit can easily be replaced. A malfunction of the valve accordingly does not require the repair or replacement of the whole device or counterpart of the disposable cartridge on the device side, but only of the valve concerned.

A preferred form of embodiment of the valve includes a fixing device for fixing the valve body in a housing. With the aid of such a fixing device, the valve can easily be inserted into the counterpart of a disposable cartridge on the device side. Spring snap rings or clamping devices, for example, are conceivable as a fixing device. A simple arrangement includes a lock nut, which can be screwed up to the outer wall of the pressure channel, which is inserted through a body wall of the counterpart of the disposable cartridge on the device side.

A seal can be provided, which serves to seal the pressure chamber against the surroundings when the valve body is fixed in the housing. It is particularly advantageous for a sealing surface also to be provided on the valve body, which sealing surface is surrounded by the sealing cap itself in such a way that the sealing cap is pressed on this sealing surface when the valve body is being fixed. A separate adjustment of the seal when fixing the valve body in the housing is then no longer necessary. The seal is also already correctly positioned when the sealing cap is fitted on the valve body.

The sealing cap can be connected with the liquid channel by means of a separate seal. A simple arrangement, however, makes provision such that a shoulder is provided on the sealing cap of the valve according to the invention, which shoulder can be pressed against the edge of the liquid channel in order to guarantee a suitable seal. With this form of embodiment, only the valve has to be aligned with respect to the fluid channel in order to guarantee an adequate seal.

In an advantageous development, the sealing cap has a projection, which restricts direct contact of the valve body with the sealing area of the sealing cap. The loading on the cap when the sealing area is pressed onto the channel is reduced by such a projection. The movement of the sealing area is not, however, impaired by the formation of a projection.

The valve according to the invention can be used in various applications for the opening and closing of fluid channels. Due to its simplicity and reliability, however, the arrangement can be used to particular advantage for controlling a fluid channel in a disposable cartridge in dialysis.

The device according to the invention for use with a disposable cartridge has at least one valve according to the invention for controlling the fluid flow rate in at least one fluid channel of the disposable cartridge. Alternatively, a device according to the invention for use with a disposable cartridge has a housing for a valve according to the invention, such that the valve according to the invention can be used for closing a fluid channel of the disposable cartridge.

A disposable cartridge according to the invention with at least one fluid channel, whose flow rate must be able to be controlled, thus requires no housings or valve seats on the disposable cartridge side to allow it to be used with a device according to the invention.

BRIEF DESCRIPTION OF THE DRAWINGS

A form of embodiment of the valve according to the invention and its application in a disposable cartridge are explained in the following with the aid of the appended figures.

They show:

FIG. 1 the cross-section through a valve according to the invention in a diagrammatic view and FIG. 2 the valve of FIG. 1 according to the invention in use in a disposable cartridge, indicated solely diagrammatically.

FIG. 1 shows valve 1 in a sectional view, which is rotation-symmetric about a vertical axis. Valve 1 consists of a valve body 2 with a pressure channel 4, which ends in a pressure chamber 16. A sealing cap 6 with a deformable area 8, which bounds pressure chamber 16, is placed over valve body 2.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Pressure channel 4 of valve body 2 is designed elongated, so that it can be inserted, for example, through the body or a wall of a counterpart of a disposable cartridge on the device side and can be screwed down with lock nut 18. A thread (not drawn) is provided for this on the outer wall of pressure channel 4. Valve body 2 has sealing surfaces 20 for sealing valve body 2 in the counterpart of the disposable cartridge on the device side. Sealing cap 6 includes protruding bulges 10, which surround valve body 2 in such a way that they lie adjacent to sealing surfaces 20 and are pressed when the valve is assembled.

The upper area of valve 1 in FIG. 1 is the area on the fluid channel side. For the fitting into the fluid channel, a shoulder 12 of sealing cap 6 is provided, such as will be explained by reference to FIG. 2. A projection 14 of sealing cap 6 lies on the end of valve body 2 on the fluid channel side.

A valve according to the invention is shown dramatically in use in FIG. 2. 28 designates the part of the disposable cartridge body in diagrammatic representation in which liquid channels 22 are stamped. 30 designates the corresponding counterpart of the disposable cartridge body on the device side, which is pressed against part 28 with fixing means (not shown) known per se.

Valve 1 is inserted into a suitably shaped housing 26 of counterpart 30 and screwed down with lock nut 18. Shoulder 12 lies adjacent to the edges of liquid channel 22. The movement of deformable area 8 when an excess pressure or partial vacuum is applied or with venting of pressure channel 4 is indicated by arrow 24. 32 indicates the direction in which the pressure is applied in order to close the valve. In FIG. 2, housing 26 in counterpart 30 is rotation-symmetric about pressure channel 4 of valve 1, whilst liquid channel 22 in the example shown extends at right angles to the plane of the figure.

Diverging from the form of embodiment shown, a cut-out for accommodating shoulder 12 can be provided either in disposable cartridge body 28 or in counterpart 30 on the device side. It is also possible for shoulder 12 to be accommodated in a suitable opening in a cover mat located between disposable body 28 and counterpart 30 on the device side.

For the sake of clarity, FIG. 2 does not show a disposable film known per se, which closes off fluid channel 22 against the surroundings. Such a disposable film can be fixed on the side of disposable body 28 that is pressed with counterpart 30 on the device side. The disposable film must be sufficiently flexible, such that it can follow the deformation of sealing area 8.

For the operation of valve 1 with a disposable cartridge, valve body 2 is inserted through housing 26 of counterpart 30 on the device side, so that pressure channel 4 extends through counterpart 30. Lock nut 18 is tightened up so that sealing bulges 10 create a seal between valve body 2 and counterpart 30. By simply screwing up lock nut 18, a tight and reliable connection of valve 1 with counterpart 30 of the disposable cartridge on the device side is thus provided.

Counterpart 30 with valve 1 is pressed with disposable cartridge body 28, whereby sealing cap 6 with shoulders 12 fits tightly with the edges of liquid channel 22. By pressing counterpart 30 on disposable cartridge body 28, several valves 1 are as a rule simultaneously fitted into corresponding liquid channels 22 at the desired points.

The dialysis liquid, for example, flows through fluid channel 22 in the opened state of valve 1. If excess pressure is applied on pressure channel 4 in the direction of arrow 32, sealing area 8 is deformed into liquid channel 22 until the latter is finally closed. The loading on the cap when pressing on the channel is minimised by projection 14, without the movement of the deformable area being significantly impaired. If a disposable film is provided on the disposable body, said disposable film is deformed together with the sealing cap into the liquid channel.

If fluid channel 22 is to be opened again, pressure channel 4 is vented and deformable area 8 of sealing cup 6 is relaxed. By applying a partial vacuum on pressure channel 4, deformable area 8 is placed against the convex curvature of pressure chamber 16 and correspondingly increases the cross-section of fluid channel 22. By simply applying or removing a pressurisation on pressure channel 4, therefore, the flow rate through fluid channel 22 can be controlled.

When the disposable cartridge is removed, the valve can be removed or replaced simply by loosening lock nut 18, e.g. for maintenance or in the event of malfunction.

The sealing cap is a simple low-cost shaped part, which on account of its closed design can easily be cleaned and thus satisfies the hygiene requirements in dialysis, but which can also easily be replaced when necessary.

When the disposable cartridge is closed again by fixing counterpart 30 on body 28, the valve fits in very well by pressing shoulder 12 with the edge of fluid channel 22. On account of the elastic stretching of deformable area 8 of sealing cap 6, there is a very good tolerance compensation both in the depth of channel 22 as well as in respect of lateral misalignment, without a significant additional expenditure of force arising. Deformable area 8 guarantees that only small forces are required to block fluid channel 22.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A valve for the closure of a fluid channel in a disposable cartridge for extracorporeal circulations, comprising a valve body having a pressure channel, and a sealing cap that cooperates with the valve body to close off said pressure channel at a proximal end of said valve body against the surroundings, said valve being designed such that a pressure chamber can be formed between the pressure channel and the sealing cap, said sealing cap having a sealing area, a shoulder, side portions that generally surround said valve body, and an inwardly directed projection at said valve end adjacent said fluid channel that extends over an upper surface of said valve body to prevent direct contact of the valve body with the sealing area, said sealing area being deformable in such a way that said fluid channel can be closed thereby and said shoulder fitting adjacent edges of said fluid channel.

2. A device for extracorporeal circulations comprising:
a disposable cartridge having at least one fluid channel configured to receive dialysis liquid;
a valve for controlling the fluid flow rate in said fluid channel, said valve including a valve body with a pressure channel and a sealing cap having a shoulder in a fixed relationship adjacent edges of said fluid channel;
a counterpart component having a housing formed therein for said valve that is generally aligned with said fluid channel when a face of said counterpart component is pressed against a face of said cartridge to assemble said device, said shoulder being compressed between said faces when said device is assembled;
said valve body being generally enclosed within said housing, and said sealing cap surrounding at least part of the valve body to close off an end of the pressure channel proximal to said valve body against the surroundings, and form a pressure chamber between the pressure channel and the sealing cap, said sealing cap having a sealing area that is deformable to close said fluid channel to control dialysis liquid flow therethrough during extracorporeal circulations.

3. The device according to claim 2, wherein said housing in said counterpart component is rotation-symmetric about the pressure channel of said valve.

4. The device according to claim 2, wherein the faces of said disposable cartridge and said counterpart component are generally parallel with one another.

5. The device according to claim 2, wherein the sealing cap has an inwardly directed projection configured to prevent direct contact of the valve body with the sealing area.

6. The device according to claim 2, wherein said sealing cap has side portions that surround an outer wall of said valve body to contact an inner wall of said housing, said side portions being generally perpendicular to said shoulder and to a space formed between said counterpart component and said cartridge by said shoulder.

7. The device according to claim 6, wherein a protruding bulge is provided at an end of said sealing cap side portions, said protruding bulge being pressed against a sealing surface on the valve body when the valve body is secured in the housing, said sealing surface and said bulge being generally perpendicular to said side portions.

8. The device according to claim 2, further comprising a fixing device configured to fix said valve body in said housing, said fixing device including a fastening component coupled to a protruding end of said pressure channel, said fastening component being in abutment with a side of said counterpart component distal from said disposable cartridge.

9. A device for extracorporeal circulations comprising a disposable cartridge with at least one fluid channel, a counterpart component pressed against said disposable cartridge and having a housing formed therein that is generally aligned with said fluid channel, and a valve inserted in said housing within said counterpart component for controlling fluid flow rate in said fluid channel, said valve having a valve body with a pressure channel therethrough and a sealing surface on an outer wall, and a sealing cap with side portions that surround at least part of said valve body within said housing, said side portions including a protruding portion that is pressed against said sealing surface of said valve body when said valve body is secured within said housing to seal said valve body in said counterpart component, said sealing cap further including a deformable sealing area that extends outside said housing to effect closure of said fluid channel.

10. The device according to claim 9, wherein said sealing cap cooperates with the valve body to close off an end of the pressure channel proximal to said valve body against the surroundings, said valve being configured such that a pressure chamber can be formed between the pressure channel and the sealing cap to deform said sealing area and close said fluid channel.

11. The device according to claim 10, further comprising a fixing device for fixing the valve body in the housing.

12. The device according to claim 11, wherein said fixing device includes a fastening component coupled to a protruding end of said pressure channel, said fastening component being in abutment with a side of said counterpart component distal from said cartridge.

13. The device according to claim 12, wherein said sealing surface is generally perpendicular to said sealing cap side portions.

14. The device according to claim 10, wherein the sealing cap is detachable from the valve body.

15. The device according to claim 9, wherein said housing in said counterpart component is rotation-symmetric about the pressure channel of said valve, and said valve body surrounded by said side portions generally corresponds in size to an opening in said counterpart component defined by said housing.

16. The device according to claim 9, wherein said sealing cap includes a shoulder compressed between said counterpart component and said disposable cartridge adjacent edges of said fluid channel.

17. The device according to claim 16, wherein said side portions extend generally perpendicular to said shoulder along an inner wall of said housing.

18. The device according to claim 17, wherein the sealing cap has a projection that extends inwardly from said shoulder to cover an upper surface of said valve body and prevent direct contact of the valve body with the sealing area.

19. The device according to claim 16, wherein interfacing surfaces of said disposable cartridge and said counterpart component are generally parallel with one another and said shoulder fits between said surfaces to maintain a spacing therebetween in areas apart from said valve while sealing said fluid channel from said spacing.

* * * * *